(12) United States Patent
Bui et al.

(10) Patent No.: US 9,636,294 B2
(45) Date of Patent: May 2, 2017

(54) LONG-WEAR MASCARA COMPOSITION

(71) Applicant: L'OREAL, Paris (FR)

(72) Inventors: Hy Si Bui, Piscataway, NJ (US);
Christopher Pang, New York, NY (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/636,411

(22) Filed: Mar. 3, 2015

(65) Prior Publication Data
US 2016/0256377 A1 Sep. 8, 2016

(51) Int. Cl.
| | | |
|---|---|---|
| *A61K 8/91* | (2006.01) | |
| *A61K 8/81* | (2006.01) | |
| *A61Q 5/06* | (2006.01) | |
| *A61Q 1/10* | (2006.01) | |

(52) U.S. Cl.
CPC .............. *A61K 8/91* (2013.01); *A61K 8/8117* (2013.01); *A61K 8/8147* (2013.01); *A61Q 1/10* (2013.01); *A61Q 5/065* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 5,874,072 A | 2/1999 | Alwattari et al. | |
| 6,110,447 A | 8/2000 | Ramin et al. | |
| 8,815,264 B2 * | 8/2014 | Wolff ....................... | A61K 8/06 424/401 |
| 2010/0028284 A1* | 2/2010 | Atis ......................... | A61Q 1/10 424/70.7 |
| 2013/0028650 A1 | 1/2013 | Atis et al. | |

FOREIGN PATENT DOCUMENTS

| | | |
|---|---|---|
| KR | 10-2011-0109899 A | 10/2011 |
| WO | WO 2010/149493 A2 | 12/2010 |

OTHER PUBLICATIONS

International Search Report and Written Opinion issued May 31, 2016 in PCT/US2016/018604.
U.S. Appl. No. 14/636,395, filed Mar. 3, 2015, Bui, et al.

* cited by examiner

*Primary Examiner* — Susan Tran
(74) *Attorney, Agent, or Firm* — Oblon, McClelland, Maier & Neustadt, L.L.P.

(57) ABSTRACT

A mascara composition including an olefin/acrylate grafted polymer and a styrene/acrylates copolymer. Preferably, the ratio of the weight amount of the olefin/acrylate grafted polymer to the weight amount of the styrene/acrylates copolymer is from about 1:3 to about 4:1.

11 Claims, 4 Drawing Sheets

LONG-WEAR MASCARA COMPOSITION

TECHNICAL FIELD

The present invention relates to a cosmetic composition for keratinous materials such as keratin fibers. The cosmetic composition is preferably a long-wear mascara composition for eyelashes.

BACKGROUND

Mascara compositions are commonly used to enhance the appearance of eyelashes. Conventional mascara compositions generally include film formers and are in the form of an emulsion including water and waxes to impart curl, volume, length, thickness, and/or color to eyelashes. Such emulsion-type mascara compositions also typically include surfactants to emulsify water and waxes. However, mascara compositions including film formers, waxes, and surfactants tend to smudge and/or flake after wearing for a certain amount of time, for example 24 hours.

Thus, there is a need for a long-lasting mascara composition which imparts an enhanced degree of curl, volume, length, thickness, and/or color for an extended period of time without smudging, breaking, or flaking.

Accordingly, one aspect of the present invention is a mascara composition which is able to address or overcome at least the aforementioned problems associated with the conventional mascara compositions. In particular, one aspect of the present invention is directed to a mascara composition which imparts an enhanced appearance to the eyelashes for an extended period of time. Another aspect of the present invention is directed to a method of making up eyelashes to enhance physical appearance of the eyelashes.

SUMMARY

According to preferred embodiments of the present invention, a mascara composition includes at least one olefin/acrylate grafted polymer and at least one styrene/acrylates copolymer. Preferably, the ratio of the weight amount of olefin/acrylate grafted polymer to the weight amount of styrene/acrylates copolymer is from about 1:3 to about 4:1.

According to preferred embodiments, the mascara composition is free of wax. Preferably, the mascara composition is not in the form of an emulsion.

According to preferred embodiments of the present invention, a method of making a mascara composition includes mixing at least one olefin/acrylate grafted polymer and at least one styrene/acrylates copolymer until dissolution. Preferably, the ratio of the weight amount of olefin/acrylate grafted polymer to the weight amount of styrene/acrylates copolymer is from about 1:3 to about 4:1.

According to preferred embodiments of the present invention, a method of improving curl of eyelashes includes applying a mascara composition including at least one olefin/acrylate grafted polymer and at least one styrene/acrylates copolymer onto eyelashes in an amount sufficient to improve the curl of eyelashes. Preferably, the ratio of the weight amount of olefin/acrylate grafted polymer to the weight amount of styrene/acrylates copolymer in the mascara composition is from about 1:3 to about 4:1.

DETAILED DESCRIPTION

Figure 1:
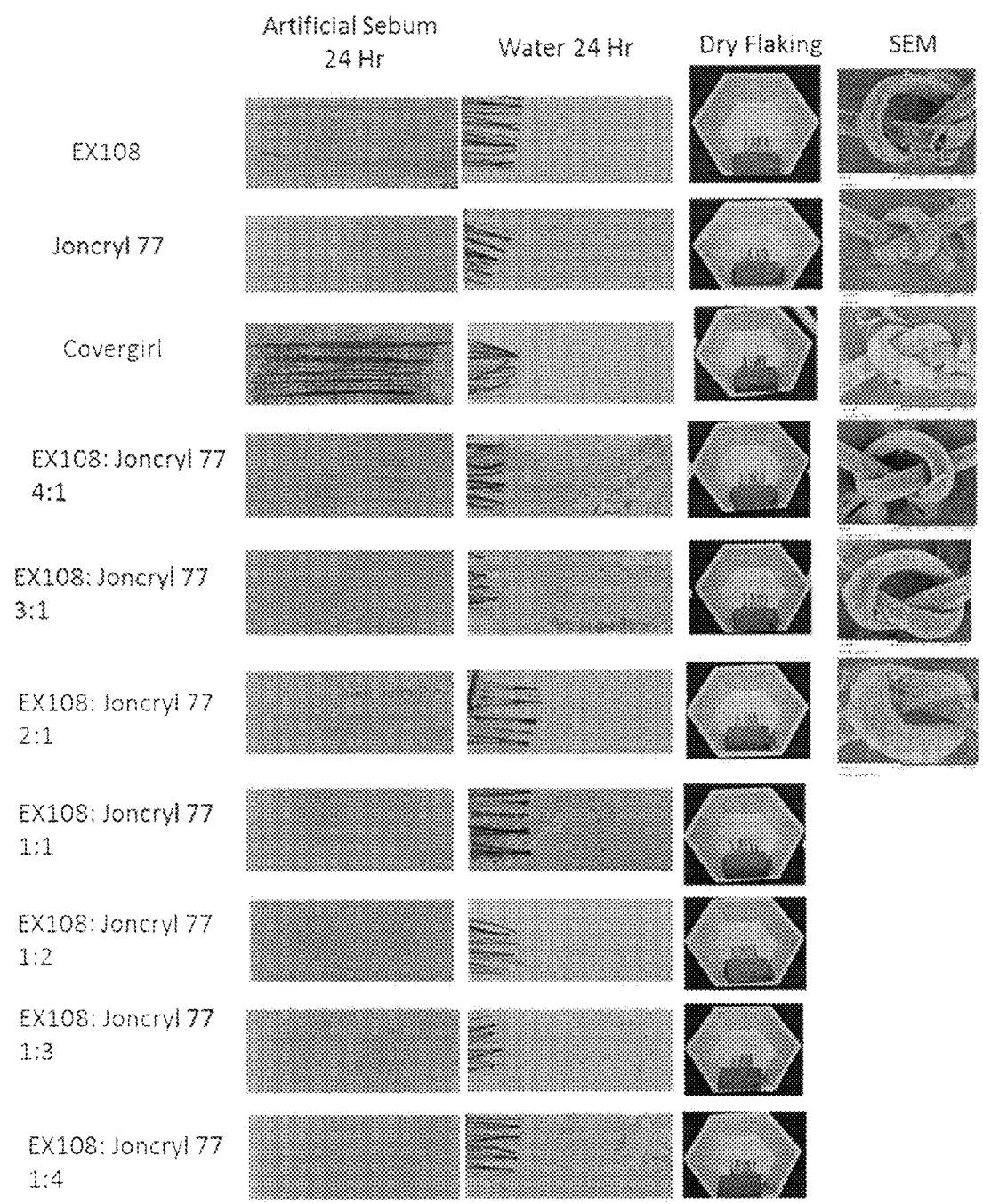
FIG. 1 shows anti-sebum, waterproof, and anti-flaking properties of the compositions of Examples 1-6, Comparative Examples 1-3, and a conventional mascara composition (Covergirl® LashBlast 24 Hr Mascara).

Unless otherwise indicated, all numbers expressing quantities of ingredients and/or reaction conditions are to be understood as being modified in all instances by the term "about." Accordingly, unless indicated to the contrary, the numerical parameters set forth in the following specification and attached claims are approximations that may vary depending upon the desired properties sought to be obtained by the present invention.

As used herein, the expression "at least one" means one or more and thus includes individual components as well as mixtures/combinations.

As used herein, the singular forms "a," "an," and "the" are intended to include the plural forms as well, unless the context clearly indicates otherwise. It will further understood that the terms "comprising," "including," and variants thereof, when used in this specification, specify the presence of stated features, elements, and/or components, but do not preclude the presence or addition of one or more other features, elements, components, and/or groups thereof.

As used herein, "mascara" and "mascara composition" mean a composition that is intended to be applied to keratinous materials, preferably keratin fibers, in particular eyelashes and/or eyebrows, further in particular eyelashes.

As used herein, "keratinous materials" include, but are not limited to, skin, nail, living keratin fibers such as head hair, eyelashes, and eyebrows, and non-living keratin fibers such as swatches, extensions, and false eyelashes. The living and non-living keratin fibers include any mammalian hair, including human hair.

As used herein, "waterproof" refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes, skin, etc. In a preferred embodiment of the present invention, little or no composition is transferred from the wearer.

As used herein, a "long-lasting" composition refers to compositions where appearance of the composition, including a film formed by the composition, remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the appearance of the composition after an extended period of time. For example, the appearance of a composition may be evaluated immediately following application to hair, skin or lips and these characteristics may then be re-evaluated and compared after a certain amount of time, such as, for example, 12 to 16 hours. Further, these characteristics may be evaluated with respect to other compositions, such as commercially available compositions.

The mascara composition and methods of the present invention can comprise, consist of, or consist essentially of the essential elements and limitations of the invention described herein, as well as any additional or optional ingredients, components, or limitations described herein or otherwise useful in personal care compositions intended for application to keratinous materials.

For purposes of the mascara composition of the present invention, the basic and novel property of a mascara composition "consisting essentially of" at least one olefin/acrylate grafted polymer and at least one styrene/acrylates copolymer is to provide the eyelashes an improved appearance for an extended period of time, without smudging, smearing, flaking, or breaking.

(Olefin/Acrylate Grafted Polymer)

According to preferred embodiments of the present invention, the mascara composition includes at least one olefin/acrylate grafted polymer. According to one of ordinary skill in the art, the term "olefin" refers to an alkene, which may be any aliphatic hydrocarbon whose molecules contain at least one carbon-carbon double bond. As used herein, the term "acrylate" refers to, for example, acrylic acid or any ester of acrylic acid, with the formula $CH_2C(R^1)COOR^2$, in which $R^1$ and $R^2$ can be hydrogen or an organic group having any number of carbon atoms. For example, $R^1$ and $R^2$ may be, but not limited to, methyl, ethyl, butyl, lauryl, and stearyl groups. The term "grafted" means, for example, physical entanglement of polymer chains and covalent grafting. The grafting may be sufficient to provide a uniform polymer emulsion with a single glass transition temperature ($T_g$) and an ability to withstand thermal and chemical attack without dissociation.

The olefin/acrylate grafted polymer that is preferably utilized in the mascara composition may be a semi-crystalline polymer. As used herein, "semi-crystalline polymer" refers to polymers that exist as viscous liquids at temperatures above the melting point of the crystals. Upon cooling, crystals nucleate and grow to fill the available volume. In a semi-crystalline polymer, some fraction of the polymer may remain un-crystallized, or, amorphous, when the polymer is cooled to room temperature. The amorphous polymer may become trapped between the growing crystals. As a result of the highly entangled (or "grafted") nature of the polymer chains, the movement of the amorphous polymer may become restricted.

Any types of olefin/acrylate grafted polymers that are cosmetically or dermatologically acceptable may be utilized in the present invention. As used herein, "cosmetically acceptable" or "dermatologically acceptable" is intended to mean that a composition is suitable for use in contact with human tissues such as keratinous materials and mucous membranes without undue toxicity, incompatibility, instability, and/or allergic response.

The olefin/acrylate grafted polymer may have a relatively low glass transition temperature, such as less than about 0° C. In some embodiments, the glass transition temperature of the olefin/acrylate grafted polymer is less than about −0.5° C., preferably less than about −5° C. The olefin/acrylate grafted polymer may have a glass transition temperature of from about −20° C. to about −0.5° C., preferably from about −10° C. to about −5° C., including all ranges and subranges therebetween.

When the olefin/acrylate grafted polymer and optionally a surfactant are dispersed in water, the dispersion may have a pH value of from about 7 to about 12, preferably from about 8 to about 10, including all ranges and subranges therebetween.

In some embodiments, the olefin/acrylate grafted polymer may be a commercially available olefin/acrylate grafted polymer dispersion, such as Syntran® EX 108 (INCI name: olefin/acrylate grafted polymer (and) sodium laureth sulfate (and) C12-15 Sec-Pareth 15) from Interpolymer. Syntran® EX 108 is available in the form of a dispersion, a latex, or an emulsion, in which an olefin/acrylate grafted polymer is dispersed in water. Syntran® EX 108 is known to include about 62% by weight of water, about 33% by weight in solid of olefin/acrylate grafted polymer, about 1% by weight of sodium laureth sulfate, and about 1% by weight of C12-15 Sec-Pareth 15. Syntran® EX 108 may have a glass transition temperature of about −6.32° C. Other non-limited examples of commercially available olefin/acrylate grafted polymer that are preferably utilized in the mascara composition include Syntran® PC5205, Syntran® PC5208, and Syntran® PC5227 from Interpolymer.

The olefin/acrylate grafted polymers that are preferably used in the present invention may be those disclosed in U.S. Pat. No. 8,865,193, contents of which are incorporated herein by reference in its entirety.

The amount of the olefin/acrylate grafted polymer(s) is preferably at least about 7% by weight, preferably at least about 15% by weight, more preferably at least about 18% by weight, relative to the total weight of the mascara composition. Preferably, the mascara composition includes the olefin/acrylate grafted polymer(s) in an amount of from about 15% to about 25% by weight, more preferably from about 18% to about 23.5% by weight, relative to the total weight of the mascara composition, including all ranges and subranges therebetween. In a particularly preferred embodiment, the mascara composition may include the olefin/acrylate grafted polymer(s) in an amount of from about 20% to about 23.5% by weight, relative to the total weight of the mascara composition.

When the mascara composition includes Syntran® EX 108, the amount of Syntran® EX 108 may be from about 20 to about 71% by weight, preferably from about 55 to about 70% by weight, more preferably from about 65 to about 70% by weight, relative to the total weight of the mascara composition, including all ranges and subranges therebetween.

(Styrene/Acrylates Copolymer)

According to preferred embodiments of the present invention, the mascara composition includes at least one styrene/acrylates copolymer. Any types of styrene/acrylates copolymers that are cosmetically and dermatologically acceptable may be utilized in the present invention.

According to one of ordinary skill in the art, the styrene/acrylates copolymer may be a polymer formed from, for example, at least two monomers of styrene and acrylate such as acrylic acid, methacrylic acid, and esters and amides of acrylic acid or methacrylic acid. As used herein, (meth)acrylate(s) is intended to mean acrylate(s) and/or methacrylate(s). A molar ratio of the styrene monomer to the acrylate monomer in the styrene/acrylates copolymer is not limited.

The styrene/acrylates copolymer may have a relatively high glass transition temperature, such as about 0° C. or higher. In some embodiments, the glass transition temperature of the styrene/acrylates copolymer may be greater than about 5° C., preferably greater than about 10° C., more preferably greater than about 14° C. The styrene/acrylates copolymer may have a glass transition temperature of from about 0° C. to about 55° C., preferably from about 10° C. to about 30° C., more preferably from about 15° C. to about 25° C., including all ranges and subranges therebetween.

In some embodiments, the styrene/acrylates copolymer may be derived from a commercially available styrene/acrylates copolymer dispersion, such as Joncryl® 77 from BASF. Joncryl® 77 is commercially available in the form of a dispersion, a latex, or an emulsion. Joncryle 77 is known to include about 45.5% of solid styrene/acrylates copolymer. Joncryl® 77 may have a glass transition temperature of about 23.41° C. Other non-limited examples of commercially available styrene/acrylates copolymer that are preferably utilized in the mascara composition include Syntran® 5288 from Interpolymer.

The solid amount of the styrene/acrylates copolymer(s) in the mascara composition is preferably from about 5% to about 22% by weight, preferably from about 5.5% to about 20% by weight, more preferably from about 5.6% to about 10% by weight, relative to the total weight of the mascara composition, including all ranges and subranges therebetween.

When the mascara composition includes Joncryl® 77, the amount of Joncryl® 77 may be from about 11 to about 50% by weight, preferably from about 12 to about 25% by weight, relative to the total weight of the mascara composition, including all ranges and subranges therebetween.

Although not intended to be bound by any theories, it is currently believed that a combination of the olefin/acrylate grafted polymer and the styrene/acrylates copolymer contributes to reduce the glass transition temperature of the mascara composition, and makes a softer film on the keratin fibers upon being dried. Thus, the mascara composition including the olefin/acrylate grafted polymer and the styrene/acrylates copolymer may have less flaking problems and comfortable wear as compared to conventional mascara compositions including, for example, film formers, waxes, and surfactants. In addition, it is believed that the semi-crystalline structure of the olefin/acrylate grafted polymer provides creamy texture to the mascara composition without using waxes. By controlling the mixing ratio of the olefin grafted polymer and the styrene/acrylates copolymer, it may be possible to control the glass transition temperature of the mascara composition to obtain desired film-softening effects.

In the mascara composition of the present invention, the ratio of the weight amount of olefin/acrylate grafted polymer to the amount of styrene/acrylates copolymer is preferably from about 1:3.5 to about 5:1, more preferably from about 1:3 to about 4:1, more preferably from about 1:2 to about 4:1, more preferably from about 1:1 to about 4:1, and particularly preferably from about 2:1 to about 4:1, including all ranges and subranges therebetween. Preferably, a weight amount of the olefin/acrylates copolymer is greater than a weight amount of the styrene/acrylates copolymer.

Further more preferably, the ratio of the amount of olefin/acrylate grafted polymer to the amount of styrene/acrylates copolymer is about 3:1 to about 4:1 including all ranges and subranges therebetween, and particularly preferably about 4:1.

When the mascara composition includes Syntran® EX 108 and Joncryl® 77, Syntran® EX 108 and Joncryl® 77 are preferably mixed in a weight ratio of from about 1:2.5 to about 6:1, more preferably from about 2:1 to about 5.5:1, including all ranges and subranges therebetween. Particularly preferred embodiments of the present invention may be prepared by mixing Syntran® EX 108 and Syntran® EX 53 in a weight ratio of from about 2.5:1 to about 5.5:1, including all ranges and subranges therebetween.

The total amount of the olefin/acrylate grafted polymer and the styrene/acrylates copolymer may be from about 15 to about 33% by weight, preferably from about 20 to about 30% by weight, relative to the total weight of the mascara composition, including all ranges and subranges therebetween.

(Wax)

According to some embodiments of the present invention, the mascara composition may optionally further include at least one wax. If present, the amount of wax may be up to about 50% by weight relative to the total weight of the mascara composition. Preferably, the amount of wax, if present, is about 10% by weight or less, about 5% by weight or less, or about 2% by weight or less, of the total weight of the mascara composition. In a particularly preferred embodiment, the mascara composition contains no wax.

As used herein, "wax" is intended to mean a lipophilic fatty compound that is solid at room temperature (about 25° C.) and atmospheric pressure (760 mmHg, i.e., 105 Pa), which undergoes a reversible solid/liquid change of state and which has a melting point of greater than 30° C., and in some embodiments, greater than about 55° C. up to about 120° C. or even as high as about 200° C. In the present invention, any waxes that are cosmetically and dermatologically acceptable may be utilized.

A variety of waxes may be useful, including waxes of animal origin, waxes of plant origin, waxes of mineral origin and waxes of synthetic origin. Examples of waxes of animal origin include beeswaxes, lanolin waxes and Chinese insect waxes.

Examples of waxes of plant origin include rice waxes, carnauba wax, candelilla wax, ouricurry wax, cork fiber waxes, sugar cane waxes, Japan waxes, sumach wax and cotton wax.

Examples of waxes of mineral origin include paraffins, microcrystalline waxes, montan waxes and ozokerites.

Examples of waxes of synthetic origin include polyolefin waxes, e.g., polyethylene waxes, waxes obtained by Fischer-Tropsch synthesis, waxy copolymers and their esters, and silicone and fluoro waxes.

Alternatively, hydrogenated oils of animal or plant origin may be used. Examples include hydrogenated jojoba waxes and hydrogenated oils which are obtained by catalytic hydrogenation of fats composed of a $C_8$-$C_{32}$ linear or non-linear fatty chain, hydrogenated sunflower oil, hydrogenated castor oil, hydrogenated copra oil, hydrogenated lanolin and hydrogenated palm oils.

The waxes may be used alone or in combination with different kind(s) of waxes. In some embodiments, the mascara composition may include at least two or at least three waxes.

The mascara composition of the present invention may include wax(es) from about 0% to about 30% by weight, preferably from about 0% to about 10% by weight, more preferably from about 0% to about 5% by weight, relative to the total weight of the mascara composition, including all ranges and subranges therebetween. In a particularly preferred embodiment, the mascara composition contains no wax.

(Surfactant)

According to the present invention, the mascara composition may optionally further include at least one surfactant. Any surfactants, including anionic, nonionic, amphoteric, and cationic surfactants, may be used in the present invention, as long as the surfactant is cosmetically or dermatologically acceptable. The surfactant may be used either singly or in combination two or more thereof.

If present, the amount of the surfactant may be up to 50% by weight relative to the total weight of the mascara composition. Preferably, the amount of the surfactant is about 10% by weight or less, about 5% by weight or less, or about 2% by weight or less, of the total weight of the mascara composition. In one embodiment, the mascara composition may contain no surfactant.

(Colorants)

According to the present invention, the mascara compositions may optionally include at least one colorant. Suitable colorants include, but are not limited to, pigments, dyes such as liposoluble dyes, nacreous pigments, and pearling agents. Typically, when the composition contains colorants, the composition may be used as a mascara composition. Alternatively, when the composition does not contain colorants, it is a clear or transparent composition which can be used as a basecoat (or topcoat) prior to (or after) application of a mascara composition to keratinous materials. However, it is possible that topcoats or basecoats could contain colorants, and/or that a mascara composition could contain little or no colorant.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration of up to 20% by weight of the total weight of the mascara composition, such as from about 0.0001% to about 6%.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, is in the composition in a concentration of up to 50% by weight relative to the total weight of the mascara composition, such as from about 0.1% to about 20% by weight, preferably from about 0.1% to about 15% by weight, including all ranges and subranges therebetween.

Representative pigments which may be used according to the present invention include white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum. If present, the pigments may be in the mascara composition in a concentration of up to 50% by weight of the total weight of the mascara composition, such as from about 0.5% to about 40% by weight, and further such as from about 2% to about 30% by weight, including all ranges and subranges therebetween. In the case of certain products, the pigments, including nacreous pigments, may, for example, represent up to about 50% by weight of the mascara composition.

(Additional Ingredients)

The mascara composition of the present invention may further include various additives desirably used in cosmetic or dermatological compositions. For example, water, dispersants, anti-oxidants, pH adjusters, preservatives, neutralizing agents, fragrances, fillers, film formers, co-solvents, plasticizers, cosmetic and dermatological active agents such as emollients, moisturizers, vitamins, UV filters, and sunscreens, and mixtures thereof can be added. A non-exhaustive listing of such ingredients can be found in the CTFA *International Cosmetic Ingredient Dictionary and Handbook*, Fourteenth Edition (2012), contents of which are incorporated herein by reference in its entirety.

One skilled in the art will take care to select the optional additional additives and/or the amount thereof such that the advantageous properties of the mascara compositions according to the present invention are not, or are not substantially, adversely affected by the envisaged addition.

These substances may be selected variously by one skilled in the art to prepare a composition which has the desired properties, for example, consistency or texture.

The combination of the olefin/acrylate grafted polymer and the styrene/acrylates copolymer may render optional the inclusion of film formers such as polymers. In a preferred embodiment, the mascara composition includes no polymer other than the olefin/acrylate grafted polymer and the styrene/acrylates copolymer. Nonetheless, the mascara compositions may include other polymers, such as film forming polymers, provided that they are compatible with the other ingredients in the inventive compositions and do not substantially, adversely affect the advantageous properties of the mascara composition. If present, the amount of the polymer(s) other than the olefin/acrylate grafted polymer and the styrene/acrylates copolymer is less than about 5% by weight, preferably less than about 3% by weight, relative to the total weight of the mascara composition.

The mascara composition of the present invention may be in any form suitable for applying on keratinous materials, in particular keratin fibers. For example, the mascara composition may be an emulsion (a water-in-oil emulsion, oil-in-water emulsion, multiple emulsion such as W/O/W and O/W/O, or nanoemulsion), a non-emulsified mixture of a water phase and an oil phase, an oil-free composition, or a water-free composition. However, particularly preferred embodiments of the present invention may be free of oil and may not be in the form of an emulsion.

The mascara composition of the present invention is intended to be applied onto keratinous materials such as keratin fibers, in particular, eyelashes or eyebrows.

According to some embodiments of the present invention, the mascara composition may have a texture suitable to be applied onto keratinous materials. The texture may be evaluated, for example, by measuring viscosity or thickness of the mascara composition. The texture may also be evaluated by experienced researchers by checking dragging properties or tackiness of the mascara composition.

Preferably, after the mascara composition is applied onto keratinous materials, the mascara composition is allowed to dry before subjecting to contact with other objects such as clothing and skin. According to one embodiment of the present invention, the mascara composition dries within a sufficiently short time for making up keratin fibers such as eyelashes and eyebrows. Depending on the amount of the mascara composition applied onto the keratinous materials, the mascara composition may completely dry within about 15 minutes, preferably about 10 minutes, more preferably about 5 minutes, after the application. As used herein, the mascara composition is considered "completely dried" when the mascara composition is not transferred to other objects upon contacting therewith.

According to preferred embodiments of the present invention, the mascara composition may have long-lasting properties and thus may stay on keratinous materials such as keratin fibers for a sufficient period of time without changing, or without substantially changing, its appearance. For example, the mascara composition may stay on the keratin fibers without breaking, cracking, flaking, smudging, and/or smearing for about 6 hours or more, preferably about 12 hours or more, more preferably about 16 hours or more, without reapplication of the mascara composition. For example, the keratin fibers on which the mascara composition is applied may have a more defined appearance, desired intensity of colors, spiking appearance, and sufficient thickness, length, and/or curl, upon application, or even after about 6 hours, about 12 hours, or preferably after about 16 hours, of application. In particularly preferred embodiments, the mascara composition may stay on the keratin fibers without breaking, flaking, smudging, and/or smearing for at least about 24 hours, preferably for at least about 48 hours, more preferably for at least for about 72 hours, without reapplication of the mascara composition.

The mascara composition may have waterproof properties. Thus, the mascara composition may repel water when exposed to water.

According to one aspect of the present invention, the mascara composition has improved cosmetic properties such as, for example, increased volume properties, increased curling properties, increased curl retention properties, increased length properties, and/or increased long wear properties.

(Methods)

Some embodiments of the present invention relate to a method of making a mascara composition including mixing at least one olefin/acrylate grafted polymer and at least one styrene/acrylates copolymer until dissolution. The olefin/acrylate grafted polymer and the styrene/acrylates copolymer may be mixed by stirring, shaking, grounding, or beating, optionally with a stirrer, a magnetic stirrer, a shaker, a homogenizer, or any other methods suitably used to mix cosmetic composition. The mixing may be carried out with or without heating or cooling the ingredients. Preferably, the ratio of the weight amount of olefin/acrylate grafted polymer to the amount of styrene/acrylates copolymer is from about 1:3.5 to about 5:1, more preferably from about 1:3 to about 4:1, more preferably from about 1:2 to about 4:1, more preferably from about 1:1 to about 4:1, and particularly preferably from about 2:1 to about 4:1, including all ranges and subranges therebetween. Preferably, a weight amount of the olefin/acrylates copolymer is greater than a weight amount of the styrene/acrylates copolymer. Further more preferably, the ratio of the amount of olefin/acrylate grafted polymer to the amount of styrene/acrylates copolymer is about 3:1 to about 4:1 including all ranges and subranges therebetween, and particularly preferably about 4:1.

One embodiment of the present invention provides a method of making up keratinous materials. The mascara composition described above is applied onto the keratinous materials. The keratinous materials may be skin, nail, or keratin fibers, preferably keratin fibers, in particular eyelashes and eyebrows. The mascara composition is applied onto the keratinous materials in an amount sufficient to make up the keratinous materials. To make up the keratin fibers, the mascara composition may be applied onto the keratin fibers in an amount sufficient to increase a volume and/or length of the keratin fibers.

One embodiment of the present invention provides a method of improving curl of keratinous materials. The mascara composition described above is applied onto the keratinous materials. The keratinous materials are preferably keratin fibers, in particular eyelashes and eyebrows. The mascara composition is applied onto the keratinous materials in an amount sufficient to improve the curl of the keratinous materials. To improve the curl of keratin fibers, the mascara composition may be applied onto the keratin fibers in an amount sufficient to increase the curl, and also a volume and/or length of the keratin fibers.

The way by which the mascara composition is applied onto the keratinous materials is not limited. Preferably, the mascara composition is applied onto keratin fibers by a brush, a wand, or a comb.

The compositions may be applied to eyelashes as needed, preferably once or twice daily, more preferably once daily and then preferably allowed to dry before subjecting to contact such as with clothing or other objects.

According to preferred embodiments of the present invention, the mascara composition is dried by leaving the mascara composition applied onto keratinous materials for a sufficient amount of time to dry the mascara composition. The mascara composition may dry within a sufficiently short time for making up keratinous materials, in particular keratin fibers such as eyelashes and eyebrows. Depending on the amount of the mascara composition applied onto the keratinous materials, the mascara composition may completely dry within about 15 minutes, preferably about 10 minutes, more preferably about 5 minutes, after the application.

One embodiment of the present invention provides a method of enhancing appearance of eyelashes. The mascara composition described above is applied onto the eyelashes. The mascara composition is applied onto the keratinous materials in an amount sufficient to enhance the physical appearance of eyelashes. In one embodiment, the mascara composition is applied onto the eyelashes in an amount sufficient to increase a volume, curl, and/or length of the eyelashes. After the mascara composition is applied, the eyelashes may have more defined appearance. After the application, the eyelashes may be longer, thicker and/or more curled as compared to the naked eyelashes.

One embodiment of the present invention provides a method of increasing curl of eyelashes. The mascara composition described above is applied onto the eyelashes in an amount sufficient to increase the curl of the eyelashes.

Another embodiment of the present invention provides a method of maintaining curls of the eyelashes for a sufficient amount of time. In preferred embodiments of the present invention, the eyelashes may maintain their curls for about 6 hours or more, preferably about 12 hours or more, more preferably about 16 hours or more. In particularly preferred embodiments, the mascara composition may maintain the curls of eyelashes without breaking, flaking, smudging, and/or smearing for at least about 24 hours, preferably for at least about 48 hours, more preferably for at least for about 72 hours, without reapplication of the mascara composition.

In the above-described methods, the mascara composition of the present invention may be applied topically to the eyelashes in an amount sufficient to make up the eyelashes, or to enhance the appearance of the eyelashes.

The mascara composition of the present invention may be a waterproof mascara composition.

The following examples are intended to illustrate the invention without limiting the scope as a result. The percentages are given on a weight basis, unless indicated otherwise.

Notwithstanding that the numerical ranges and parameters setting forth the broad scope of the invention are approximations, the numerical values set forth in the specific examples are reported as precisely as possible. Any numerical value, however, inherently contain errors necessarily resulting from the standard deviation found in their respective measurements.

EXAMPLES

Mascara Compositions

Mascara compositions of Examples 1 to 6 and Comparative Examples 1 to 3 were prepared from the ingredients shown in Table 1 below. The numbers shown in the parentheses in the amounts of "olefin/acrylate grafted polymer (and) sodium laureth sulfate (and) C12-15 Sec-Pareth 15" and "styrene/acrylates copolymer" indicate the amounts of olefin/acrylate grafted polymer and styrene acrylates copolymer contained in Syntran® EX 108 and Joncryl® 77, respectively, with respect to the total amount of the mascara composition.

The mascara compositions of Examples 1 to 6 and Comparative Examples 1 to 3 were prepared by simultaneously mixing all ingredients with a high-speed mixer at 25 rpm for 3 minutes. The mixing was conducted at room temperature.

(i) In Vitro Testing of Long Lasting Properties

Each of the mascara compositions of Examples 1 to 6 and Comparative Examples 1 to 3 were applied on fake eyelashes and then submerged into artificial sebum or water for 24 hours. The fake eyelashes were then brushed on water color papers 10 times to see if the mascara pigment transfers from the fake eyelashes to the water color paper. For comparison, a conventional mascara composition including a wax and a surfactant (Covergirl® LashBlast 24 Hr Mascara) was also applied on the fake eyelashes, submerged into artificial sebum or water, and brushed on the water color paper, in the same manner as described above. The results are shown in FIG. 1.

In FIG. 1, "EX108" indicates Comparative Example 1, "Joncryl77" indicates Comparative Example 3, "Covergirl" indicates Covergirl® LashBlast 24 Hr Mascara, "EX108:Joncryl77 4:1" indicates Example 1, "EX108:Joncryl77 3:1" indicates Example 2, "EX108:Joncryl77 2:1" indicates Example 3, "EX108:Joncryl77 1:1" indicates Example 4, "EX108:Joncryl77 1:2" indicates Example 5, "EX108:Joncryl77 1:3" indicates Example 6, and "EX108:Joncryl77 1:4" indicates Comparative Example 2.

Examples 1 to 3, Comparative Examples 1 and 3, and the conventional mascara composition (Covergirl® LashBlast 24 Hr Mascara) were also applied to untreated human hair samples and completely dried. The hair samples were then tied to see if the mascara films formed on the hair samples crack or break when the hair is bent.

As shown in FIG. 1, the mascara compositions of Examples 1 to 6 showed improved sebum and water resis-

TABLE 1

|  | Comp. 1 | Example 1 | Example 2 | Example 3 | Example 4 | Example 5 | Example 6 | Comp. 2 | Comp. 3 |
| --- | --- | --- | --- | --- | --- | --- | --- | --- | --- |
| Olefin/acrylate grafted polymer (and) sodium laureth sulfate (and) C12-15 Sec-Pareth 15* (olefin/acrylate grafted polymer) | 87.88 (29.0) | 70.3 (23.2) | 65.91 (21.8) | 58.59 (19.3) | 43.94 (14.5) | 29.29 (9.7) | 21.97 (7.3) | 17.58 (5.8) | 0 (0) |
| Styrene/acrylates copolymer dispersion** (styrene/acrylate grafted polymer) | 0 (0) | 12.75 (5.8) | 15.93 (7.3) | 21.25 (9.7) | 31.87 (14.5) | 42.49 (19.3) | 47.8 (21.8) | 50.99 (23.2) | 63.74 (30.6) |
| Pigment | 11.55 | 11.55 | 11.55 | 11.55 | 11.55 | 11.55 | 11.55 | 11.55 | 11.55 |
| Water | 0.57 | 5.4 | 6.61 | 8.61 | 12.64 | 16.67 | 18.68 | 19.88 | 24.71 |
| (olefin/acrylate):(styrene/acrylates copolymer)*** | 1:0 | 4:1 | 3:1 | 2:1 | 1:1 | 1:2 | 1:3 | 1:4 | 0:1 |
| film former | 29 | 29 | 29 | 29 | 29 | 29 | 29 | 29 | 29 |
| Total water**** | 59.45 | 59.45 | 59.45 | 59.45 | 59.45 | 59.45 | 59.45 | 59.45 | 59.45 |

*Syntran ® EX 108
**Joncryl ® 77
***(olefin/acrylate):(styrene/acrylates copolymer) indicates a weight ratio of the amount of olefin/acrylate grafted polymer to the amount of styrene/acrylates copolymer.
****Total water indicates a total amount of water in the composition including water contained in polymer dispersions.

tance. The film of dried mascara compositions of Examples 1 to 6 showed less dry flaking, as compared to those of Comparative Examples 1 to 3 and the conventional mascara composition (Covergirl®). Examples 1 and 2 (indicated in FIG. 1 as "EX108: Joncryl 77 4:1" and "EX108: Joncryl 77 3:1," respectively) showed particularly improved resistances to sebum and water.

The SEM images of the hair samples treated with Examples 1 to 3, Comparative Examples 1 and 3, and the conventional mascara composition are shown in the rightmost column in FIG. 1. Those SEM images demonstrate that the dried films of the mascara compositions of Comparative Examples 1 and 3 and the conventional mascara composition showed cracking and/or flaking upon bending the hair, while those of Examples 1 to 3 did not show cracking and flaking of the films.

(i) In Vivo Testing of Long Lasting Properties

Example 1, Comparative Examples 1 and 3, and the conventional mascara composition were also tested in vivo to evaluate their long lasting properties.

Six panellists applied each mascara compositions on their eyelashes and wore the compositions for up to 72 hours until the mascara composition smudged, broke, flaked, and/or faded.

The panellists indicated that Example 1 did not smudge, break, flake, and/or fade after 24 hours, 48 hours, and 72 hours of application.

The panellists indicated that Comparative Example 1 did not smudge, break, flake, and/or fade after 24 hours of application, but smudged after 48 hours of application. The film formed by Comparative Example 1 was too soft and easy to be removed by rubbing.

The panellists indicated that Comparative Example 3 did not smudge, break, flake, and/or fade after 24 hours and 48 hours of application, but smudged after 72 hours of application. The film formed by Comparative Example 3 was brittle and easily cracked.

The panellists indicated that the conventional mascara composition including a wax and surfactant smudged after 24 hours of application.

The results indicate that, by combining the olefin/acrylate grafted polymer and the styrene/acrylates copolymer, a softer film may be prepared on the eyelashes upon drying the composition. The softer film may provide improved wear for the users while maintaining good water and sebum resistances.

Mixture of an Olefin/Acrylate Grafted Polymer and a Styrene/Acrylates Copolymer

To evaluate thermal properties of compositions including olefin/acrylate grafted polymer and a styrene/acrylates copolymer, Syntran® EX 108 was mixed with Joncryl® 77 with various mixing ratios. The mixing ratios of Syntran® EX 108 and Joncryl® 77, and the glass transition temperatures of each of the mixtures are shown in Table 2. In Table 2, the mixing ratios of Syntran® EX 108 and Joncryl® 77 are indicated as the amount ratios of olefin/acrylate grafted polymer to styrene/acrylates copolymer contained in Syntran® EX 108 and Joncryl® 77, respectively. The mixtures were analysed with DSC Q2000 (differential scanning calorimeter), TA instrument. Each of the mixtures were cast onto a Teflon-coated petri dish and dried for a week with 25 m² air flow to form a dried film. The dried films were then heated at 10° C./min from −80° C. to 125° C. (Cycle 1), cooled at 10° C./min from 125° C. to −80° C. (Cycle 2), and heated at 10° C./min from −80° C. to 150° C. (Cycle 3).

TABLE 2

| Weight ratio ((olefin/acrylate grafted polymer):(styrene/acrylates copolymer)) | $T_g$ (° C.) |
|---|---|
| 0:1 | 23.41 |
| 1:4 | 19.37 |
| 1:3 | 19.45 |
| 1:2 | 20.36 |
| 1:1 | 17.42 |
| 2:1 | 12.07 |
| 3:1 | 5.12 |
| 4:1 | 1.19 |
| 1:0 | −6.32 |

Figure 2A:
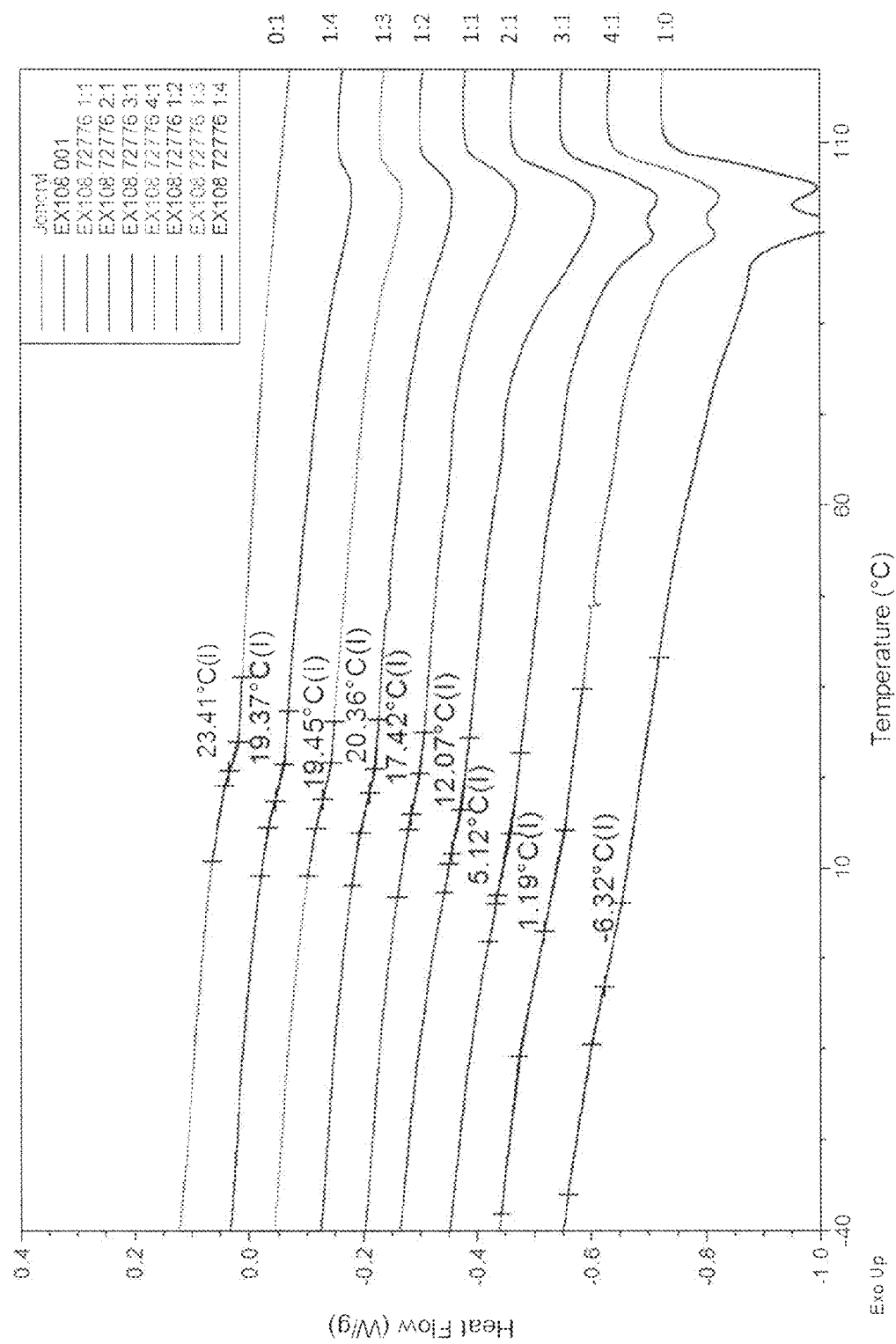
FIG. 2A is a graph showing the DSC measurement result when heating mixtures of Syntran® EX108 and Joncryl® 77 with various mixing ratios. The mixing ratio indicates a weight ratio of (Syntran® EX108): (Joncryl® 77).
Figure 2B:
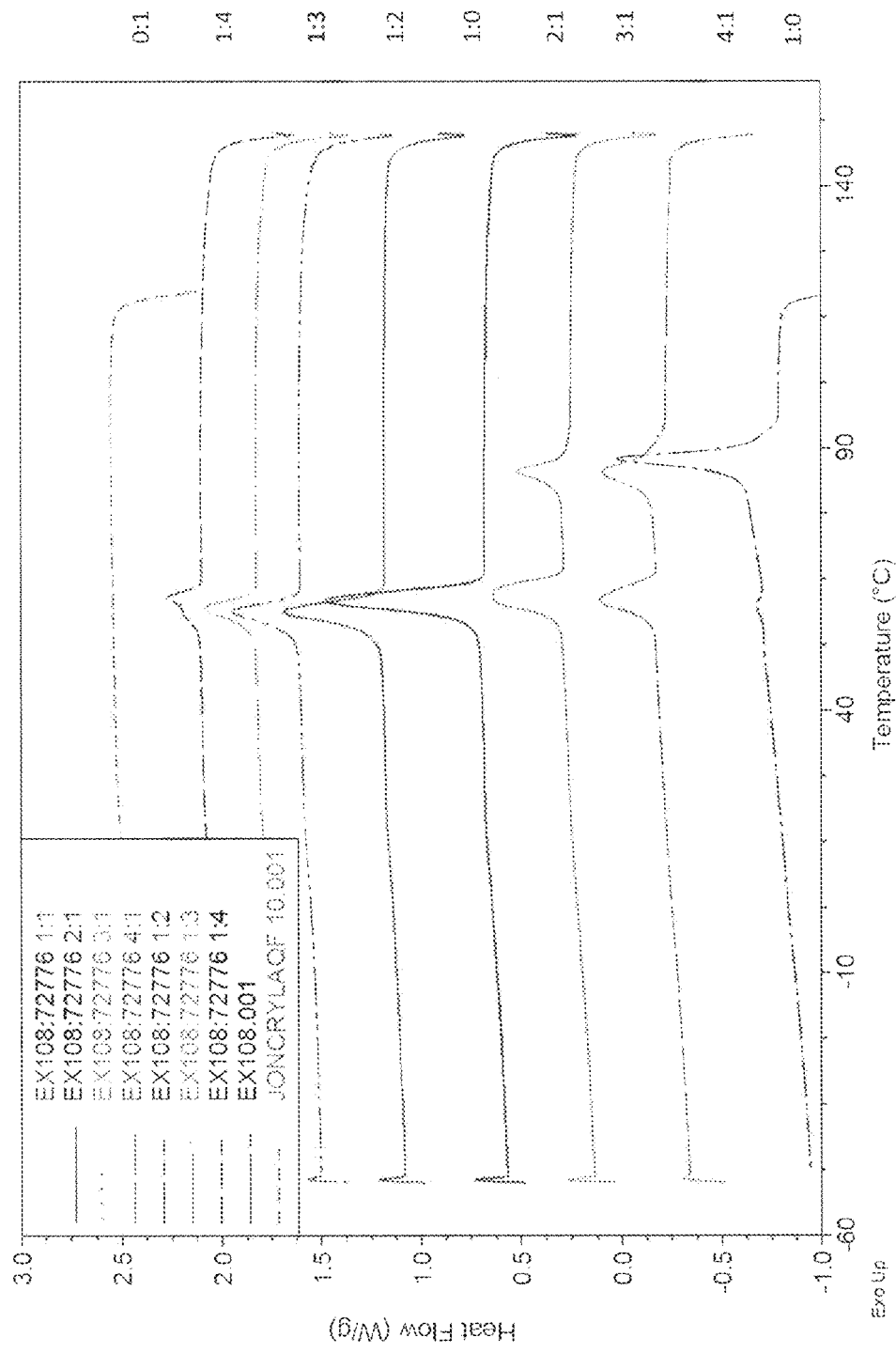
FIG. 2B is a graph showing the DSC measurement result when cooling mixtures of Syntran® EX108 and Joncryl® 77 with various mixing ratios. The mixing ratio indicates a weight ratio of (Syntran® EX108): (Joncryl® 77).
Figure 3:
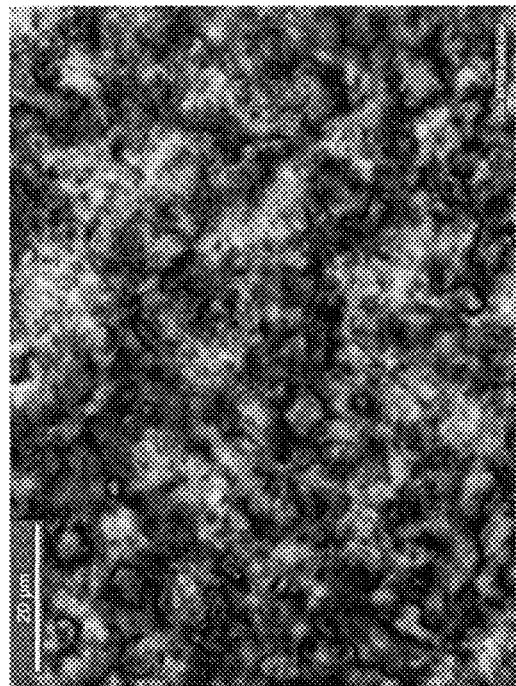
FIG. 3 shows microscopic images of crystalline structures formed by cooling Syntran® EX108 from 130° C. to 25° C. at a rate of 2° C./min.
Figure 3:
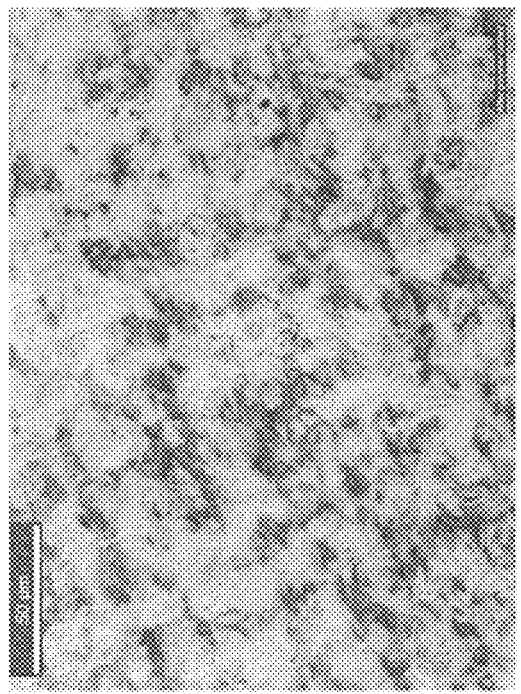
Figure 3:
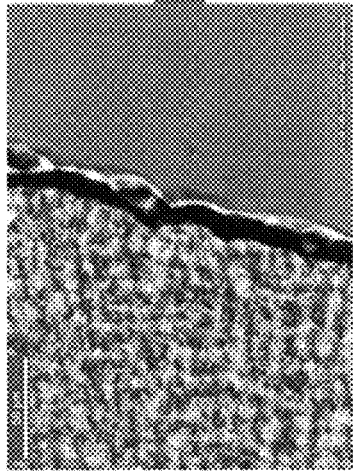

As shown in Table 2 and FIG. 2A, as the concentration of Syntran® EX108 in the mixture increased, the film formed by the mixture of Syntran® EX 108 and Joncryl® 77 became softer and the glass transition temperature decreased from 23.41° C. to 1.19° C. As shown in FIG. 2B, in the mixtures of Syntran® EX 108 and Joncryl® 77, uniform crystals formed at temperatures of from 52.5 to 65° C. As the weight amount of Syntran® EX 108 in the mixture increased to more than 67% (as the weight amount of Joncryl® 77 decreased to less than 33%), an additional crystallization peak appeared at 80 to 90° C. Such results appear to be caused by the formation of small crystals from Syntran® EX 108, as shown in FIG. 3.

The invention claimed is:

1. A mascara composition, comprising:
   at least one olefin/acrylate grafted polymer; and
   at least one styrene/acrylates copolymer,
   wherein a ratio of a weight amount of the olefin/acrylate grafted polymer to a weight amount of the styrene/acrylates copolymer is from 1:3 to 4:1.

2. The mascara composition of claim 1, wherein the mascara composition is free of wax.

3. The mascara composition of claim 1, wherein the mascara composition is not in the form of an emulsion.

4. The mascara composition of claim 1, wherein
   the weight amount of the olefin/acrylate grafted polymer is from 15 to 25% relative to the total weight of the mascara composition, and
   the weight amount of the styrene/acrylates copolymer is from 5 to 10% relative to the total weight of the mascara composition.

5. The mascara composition of claim 1, wherein the olefin/acrylate grafted polymer is a semi-crystalline polymer.

6. The mascara composition of claim 1, wherein a ratio of the weight amount of the olefin/acrylate grafted polymer to the weight amount of the styrene/acrylates copolymer is from 2:1 to 4:1.

7. The mascara composition of claim 1, wherein the ratio of the weight amount of the olefin/acrylate grafted polymer to the weight amount of the styrene/acrylates copolymer is from 3:1 to 4:1.

8. The mascara composition of claim 1, wherein the olefin/acrylate grafted polymer has a glass transition temperature of less than 0° C.

9. The mascara composition of claim 1, wherein the styrene/acrylates copolymer has a glass transition temperature of 0° C. or more.

10. A method of increasing thickness of eyelashes, comprising:
    applying a mascara composition comprising at least one olefin/acrylate grafted polymer and at least one styrene/acrylates copolymer onto eyelashes in an amount sufficient to increase thickness of eyelashes, wherein a ratio of a weight amount of the olefin/acrylate grafted polymer to a weight amount of the styrene/acrylates copolymer in the mascara composition is from 1:3 to 4:1.

11. A method of making a mascara composition, comprising mixing at least one olefin/acrylate grafted polymer and at least one styrene/acrylates copolymer until dissolution, wherein a ratio of a weight amount of the olefin/acrylate grafted polymer to a weight amount of the styrene/acrylates copolymer mixed in the mascara composition is from 1:3 to 4:1.

* * * * *